United States Patent [19]

Shay et al.

[11] Patent Number: 5,833,832
[45] Date of Patent: Nov. 10, 1998

[54] PREPARATION OF ONIUM HYDROXIDES IN AN ELECTROCHEMICAL CELL

[75] Inventors: Christopher D. Shay; Hossein Sharifian, both of Austin, Tex.

[73] Assignee: Sachem, Inc., Austin, Tex.

[21] Appl. No.: 704,898

[22] Filed: Aug. 30, 1996

[51] Int. Cl.$^6$ ............................. C25B 3/00; C02F 1/469
[52] U.S. Cl. ............... 205/413; 205/344; 205/431; 205/445; 205/770; 204/523; 204/537; 204/541
[58] Field of Search ............................. 205/344, 431, 205/437, 445, 413, 703, 770; 204/522, 523, 530, 534, 537, 541

[56] References Cited

U.S. PATENT DOCUMENTS

| | | | |
|---|---|---|---|
| 3,402,115 | 9/1968 | Campbell et al. | 204/180 |
| 3,523,068 | 8/1970 | Eisenhauer et al. | 204/72 |
| 4,391,680 | 7/1983 | Mani et al. | 204/98 |
| 4,394,226 | 7/1983 | Wade et al. | 204/72 |
| 4,521,285 | 6/1985 | De Witt et al. | 205/431 |
| 4,578,161 | 3/1986 | Buonomo et al. | 204/102 |
| 4,740,281 | 4/1988 | Chlanda et al. | 204/151 |
| 4,904,357 | 2/1990 | Sharirian et al. | 204/73 R |
| 4,938,854 | 7/1990 | Sharifian et al. | 204/130 |
| 5,006,211 | 4/1991 | Paleologon et al. | 204/182.4 |
| 5,198,086 | 3/1993 | Chlanda et al. | 204/182.4 |
| 5,207,879 | 5/1993 | Butterworth | 204/182.4 |
| 5,240,579 | 8/1993 | Kadem | 204/182.4 |
| 5,250,159 | 10/1993 | Butterworth | 204/98 |
| 5,286,354 | 2/1994 | Baid et al. | 204/86 |
| 5,358,609 | 10/1994 | Drachett | 204/84 |
| 5,389,211 | 2/1995 | Sharifian et al. | 204/72 |
| 5,391,268 | 2/1995 | Kaczur et al. | 204/102 |
| 5,397,445 | 3/1995 | Umemura et al. | 204/182.4 |
| 5,447,610 | 9/1995 | Sharifian | 204/101 |

FOREIGN PATENT DOCUMENTS

| | | |
|---|---|---|
| 06299385 | 10/1994 | Japan . |
| 6299385 | 10/1994 | Japan . |

OTHER PUBLICATIONS

JAPIO abstract of JP06299385 (Tetsuo et al.) Oct. 25, 1994.

International Search Report for PCT Application PCT/US97/15071 mailed Nov. 19, 1997.

Genders, *Watts New*, "Electrochemical Splitting", vol. 1, No. 1, Sep. 1995.

Chang, *Journal of Applied Electrochemistry*, "Conversion of Etthylene Diamine Dihydrochloride . . . ", 9(1979), 731–736, Nov. 1978.

*Primary Examiner*—Terrence Till
*Assistant Examiner*—Alex Noguerola
*Attorney, Agent, or Firm*—Renner, Otto, Boisselle & Sklar

[57] ABSTRACT

A process is described for preparing onium hydroxides from the respective onium salts and for purifying onium hydroxides in an electrochemical cell. In one example, the present invention relates to a process for preparing onium hydroxides from the corresponding onium salts which comprises the steps of: (A) providing a cell comprising an anode, a cathode and one or more unit cells assembled for operational positioning between the anode and the cathode, each unit cell comprising: (A-1) four compartments defined by, in sequence beginning at the anode, a bipolar membrane, a first divider and a second divider, said bipolar membrane having an anion selective side facing the anode and a cation selective side facing the cathode.

26 Claims, 4 Drawing Sheets

PREPARATION OF ONIUM HYDROXIDES IN AN ELECTROCHEMICAL CELL

FIELD OF THE INVENTION

This invention relates to a method of preparing onium hydroxides and to a method of purifying onium hydroxides. More particularly, the invention relates to the method of preparing and purifying onium hydroxides such as quaternary ammonium hydroxides, quaternary phosphonium hydroxides, and tertiary sulfonium hydroxides from the respective onium salts (or the hydroxide) in an electrochemical cell containing a bipolar membrane.

BACKGROUND OF THE INVENTION

Quaternary ammonium hydroxides such as tetramethylammonium hydroxide (TMAH) and tetraethylammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxide, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium and potassium, and halides such as chloride, bromide, iodide, etc. Particularly in recent years, there has been an increasing demand for quaternary ammonium hydroxides having a high purity.

Quaternary ammonium hydroxides such as TMAH and TEAH have been produced by various techniques. Generally, the quaternary ammonium hydroxides are manufactured by electrolyzing a salt of a quaternary ammonium compound in an electrochemical cell containing one or more cation-exchange membranes. The quaternary ammonium salts used in such preparations include halide salts, carboxylate salts, carbonate salts and sulfate salts.

Electrochemical cells use electrical current as a means to cause the movement of ions in solution. Among the prior art patents which describe the preparation of quaternary ammonium hydroxides by electrolyzing a salt of a quaternary ammonium compound are U.S. Pat. Nos. 4,578,161 (Buonomo et al); 4,394,226 (Wade et al); 3,523,068 (Eisenhauer et al); and 3,402,115 (Campbell et al). Electrodialysis processes are well known in the art and are typically carried out in a stack arrangement comprising a plurality of flat sheet membranes. A stack consists of electrodes (anode arid cathode) at either end and a series of membranes and gaskets which are open in the middle to form a multiplicity of compartments separated by the membranes. Usually, a separate solution is supplied to the compartments containing the electrodes, and special membranes may be placed next to the electrode containing compartments in order to prevent mixing of the process streams with the electrode streams. The stack between the electrode compartments comprises an assembly of repeating series of units of different membranes with solution compartments between adjacent membranes. This repeating unit is called a unit cell. Each unit cell is arranged to provide a plurality of parallel flow paths or channels therebetween. Solution is typically supplied to the compartments by internal manifolds formed as a part of the gaskets or by a combination of internal and external manifolds. The stacks can include more than one type of unit cell, and streams may be fed from one stack to another in order to optimize process efficiency.

Treatment of aqueous salt streams by electrodialysis to form acid and/or base from the salt is known. The aqueous salt stream is fed to an electrodialytic water-splitting apparatus which comprises an electrodialysis stack and a means for electrodiatically splitting water. A useful means to split water to $H^+$ and $OH^-$ is a bipolar membrane. Bipolar membranes are comprised of an anion-selective layer and a cation-selective layer of ion exchange material. In order for the membrane to function as a water splitter, the layers must be arranged so that the anion layer in each membrane is closer to the anode than the cation layer. A direct current passed through the membrane in this configuration will cause water splitting with hydroxyl ions being produced on the anode side and a corresponding number of protons being produced on the cathode side of the membrane. The disassociated salt cations pass through cation selective membranes and move toward the cathode, and the disassociated salt anions pass through the anion selective membrane and move toward the anode.

Electrodialytic water splitting in a two-compartment cell has been disclosed in, for example, U.S. Pat. No. 4,391,680 relating to the generation of strongly acidified sodium chloride and aqueous sodium hydroxide from aqueous sodium chloride. Three compartment electrodialyltic water splitters are disclosed to be comprised of alternating bipolar, anion and cation exchange membranes in, for example, U.S. Pat. No. 4,740,281.

U.S. Pat. No. 5,397,445 describes various electrodialytic configurations employing bipolar, anionic and cationic membranes for producing an acid and/or an alkali metal hydroxide from a neutral salt. U.S. Pat. No. 5,198,086 also describes various configurations or electrodialytically converting salt, the salt of a strong base and a weak acid to a base with improved purity.

SUMMARY OF THE INVENTION

A process is described for preparing onium hydroxides from the respective onium salts and for purifying onium hydroxides in an electrochemical cell. In one embodiment, the present invention relates to a process which comprises the steps of: (A) providing a cell comprising an anode, a cathode and one or more unit cells assembled for operational positioning between the anode and the cathode, each unit cell comprising: (A-1) four compartments defined by, in sequence beginning at the anode, a bipolar membrane, a first divider and a second divider, said bipolar membrane having an anion selective side facing the anode and a cation selective side facing the cathode; or (A-2) four compartments defined by, in sequence beginning at the anode, a first divider, a second divider, and a bipolar membrane having an anion selective side facing the anode and a cation selective side facing the cathode; or (A-3) five compartments defined by, in sequence beginning at the anode, a first bipolar membrane, a first divider, a second divider, and a second bipolar membrane, each of said bipolar membranes having an anion selective side facing the anode and a cation selective side facing the cathode; or (A-4) five compartments defined by, in sequence beginning at the anode, a bipolar membrane, a first divider, a second divider, and a third divider, said bipolar membrane having an anion selective side facing the anode and a cation selective side facing the cathode; or (A-5) six compartments defined by, in sequence beginning at the anode by a first bipolar membrane, a first divider, a second divider, a third divider, and a second bipolar membrane, each of said bipolar membranes having an anion selective side facing the anode and a cation selective side facing the cathode; (B) charging a solution of an onium salt or the onium hydroxide to be purified to the compartment in each unit cell formed by the first and second dividers; (C) charging a liquid electrolyte to the other compartments of each unit cell; (D) passing a current through the cell to produce an onium hydroxide in the compartment in each unit cell formed by one of the dividers on the anode side and a bipolar membrane on the cathode side, or the compartment formed by a divider and the cathode; and (E) recovering the onium hydroxide from said compartments.

DESCRIPTION OF THE PREFERRED EMBODIMENTS

Figure 1:
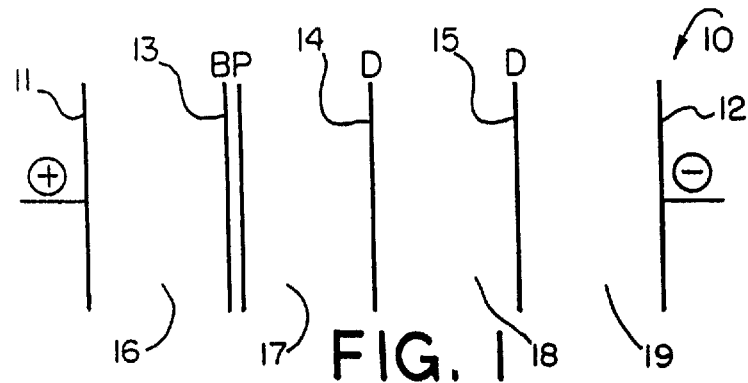
FIG. 1 is a schematic representation of a four-compartment electrolytic cell containing one unit cell useful for generating onium hydroxides in accordance with the invention.

The onium hydroxides which are prepared in accordance with the process of the present invention are derived from the corresponding onium salts. The onium salts may generally be characterized by the formula $$A^+X^-$$

wherein $A^+$ is an onium cation and $X^-$ is an anion of an acid such as a halide ion, a sulfate, hydrogen sulfate or alkylsulfate anion, a carboxylate anion, a nitrate anion, a carbonate or alkyl carbonate anion, a phosphate, hydrogen phosphate or dihydrogen phosphate anion, etc. Halide, sulfate, formate and carbonate anions are preferred, and halide anions are most preferred. The halide ions include chloride, bromide, fluoride and iodide ions. An example of an alkyl sulfate anion is methyl sulfate ($CH_3SO_4$—), and examples of carboxylic acid anions include the formate and acetate anions.

In one preferred embodiment of the present invention, the onium salts are characterized by the above formula where $A^+$ is a quaternary ammonium, quaternary phosphonium or a tertiary sulfonium cation.

The quaternary ammonium and quaternary phosphonium salts may be characterized by the formula

wherein A is a nitrogen or phosphorus atom, $X^-$ is an anion of an acid as described above, y is a number equal to the valence of X, and $R^1$, $R^2$, $R^3$ and $R^4$ are each independently alkyl groups containing from 1 to about 20 carbon atoms, hydroxyalkyl or alkoxyalkyl groups containing from 2 to about 20 carbon atoms, aryl groups, or hydroxyaryl groups, or $R^1$ and $R^2$ together with A may form a heterocyclic group provided that if the heterocyclic group contains a C=A group, $R^3$ is the second bond.

The alkyl groups may be linear or branched, and specific examples of alkyl groups containing from 1 to 20 carbon atoms include methyl, ethyl, propyl, butyl, pentyl, hexyl, heptyl, octyl, isooctyl, nonyl, octyl, decyl, isodecyl, dodecyl, tridecyl, isotridecyl, hexadecyl and octadecyl groups. $R^1$, $R^2$, $R_3$ and $R^4$ also may be hydroxyalkyl groups such as hydroxyethyl and the various isomers of hydroxypropyl, hydroxybutyl, hydroxypentyl, etc. In one preferred embodiment, the R groups are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

Examples of quaternary ammonium halides representative of Formula I which can be treated in accordance with the process of the present invention to form quaternary ammonium hydroxides include tetramethylammonium chloride, tetramethylammonium bromide, tetraethylammonium chloride, tetraethylammonium bromide, tetrapropylammonium bromide, tetraethylammonium bromide, tetra-n-octylammonium bromide, trimethylhydroxyethylammonium chloride, trimethylmethoxyethylammonium chloride, dimethyldihydroxyethylammonium chloride, methyltrihydroxyethylammoniumchloride, phenyltrimethylammoniumchloride, phenyltriethylammonium chloride, benzyltrimethylammonium chloride, benzyltriethylammonium chloride, dimethylpyrolidinium bromide, dimethylpiperidinium bromide, diisopropylimidazolinium bromide, N-alkylpyridinium bromide, etc. The corresponding quaternary ammonium sulfate, carbonate, phosphate and formate salts also can be used.

Examples of quaternary phosphonium halides representative of Formula I which can be used in the process of the present invention to form quaternary phosphonium hydroxides include tetramethylphosphonium bromide, tetraethylphosphoniumbromide, tetrapropylphosphoniumbromide, tetrabutylphosphonium bromide, trimethylhydroxyethylphosphonium bromide, dimethyldihydroxyethylphosphonium bromide, methyltrihydroxyethylphosphonium bromide, phenyltrimethylphosphonium bromide, phenyltriethylphosphonium bromide and benzyltrimethylphosphonium bromide. The corresponding chloride, sulfate, phosphate, carbonate and formate salts also can be converted to the corresponding hydroxides.

In another embodiment, the tertiary sulfonium salts which can be used in accordance with this invention to form tertiary sulfonium hydroxides may be represented by the formula

(II)

wherein $X^-$ is an anion of an acid is described above, y is a number equal to the valence of X, and $R^1$, $R^2$ and $R^3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R_1$ and $R_2$ together with S may form a heterocyclic group provided that if the heterocyclic group contains a C=S group, $R_3$ is the second bond.

Examples of the halides represented by Formula II include trimethylsulfonium chloride, trimethylsulfonium bromide, triethylsulfonium bromide, tripropylsulfonium bromide, etc.

In one preferred embodiment, the quaternary ammonium salt is represented by the formula

(III)

wherein $R^1$, $R^2$, $R^3$ and $R^4$ are each independently alkyl groups containing from 1 to 10 carbon atoms, hydroxyalkyl or alkoxyalkyl groups containing from 2 to about 10 carbon atoms, aryl groups or hydroxyaryl groups, X is an anion of an acid, and y is a number equal to the valence of X.

Specific examples of alkyl groups containing from 1 to 10 carbon atoms include methyl, ethyl, propyl, butyl, pentyl, hexyl, heptyl, octyl, nonyl, and decyl groups. $R^1$, $R^2$, $R^3$ and $R^4$ also may be hydroxyalkyl groups such as hydroxyethyl and the various isomers of hydroxypropyl, hydroxybutyl, hydroxypentyl, etc. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

Specific examples of the anion $X^-$ include the halide anions such as fluoride, chloride, bromide and iodide, sulfate anions, formate anions, acetate anions, carbonate anions, etc. The process of the present invention is particularly useful when the salt is a halide.

In one preferred embodiment, the R groups are alkyl groups containing 1 to 4 carbon atoms and hydroxyalkyl groups containing from 2 to 4 carbon atoms. Most often, the quaternary ammonium salts treated in accordance with the process of the present invention will be tetramethylammonium chloride, tetraethylammonium chloride, tetra n-propylammonium chloride or tetra-n-butylammonium chloride.

In accordance with one embodiment the process of the present invention, the onium salts such as those described above are converted to onium hydroxides in an electrochemical cell. In another embodiment of the invention, onium hydroxides can be purified in an electrochemical cell. For example impure onium hydroxide containing, for example, metals, halides, etc. can be purified by the process of this invention.

The conversion process and the purification of onium hydroxides in accordance with this invention may be by electrolysis in an electrolytic cell or by electrodialysis in an electrodialytic cell. The electrochemical cells generally comprise an anode, a cathode, and one or more unit cells assembled for operational positioning between the anode and the cathode. A number of electrolytic and electrodialytic cells containing various unit cells and multiple unit cells are described herein which are useful in the process of the present invention. The unit cells may comprise four or more compartments defined by the anode, cathode, one or more bipolar membranes and one or more dividers or separators which may be (1) nonionic microporous diffusion barriers such as screens, filters, diaphragms, etc., of controlled pore size or pore size distribution allowing certain ions to pass through the divider or separator, or (2) ionic dividers or separators such as anion selective membranes and cation selective membranes which are preferred since their use generally results in the production of onium hydroxides of higher purity and in higher yield. The various dividers useful in the electrochemical cells used in the invention are described more fully below. Several electrolyte cells useful in the present invention are described below. In the following embodiments which generally describe the conversion of onium salts to onium hydroxide, the purification of onium hydroxides of the process of the invention can be illustrated by replacing the onium salt charged to the cell by an impure onium hydroxide. The onium hydroxide which is recovered is of a higher purity than the hydroxide that was charged to the cell.

In one embodiment, a unit cell used in this invention comprises four compartments defined by, in sequence beginning at the anode, a bipolar membrane, a first divider and a second divider, said bipolar membrane having an anion selective side facing the anode and a cation selective side forming the cathode. This arrangement of a unit cell is referred to herein as the BDD arrangement.

An electrochemical cell utilizing the BDD unit cell arrangement is illustrated in FIG. 1 which is a schematic representation of an electrolysis cell 10 comprising an anode 11, a cathode 12 and a unit cell which comprises in sequence, beginning at the anode 11, a bipolar membrane 13, a first divider 14, and a second divider 15. The bipolar membrane 13 has an anion selective side (not shown) facing the anode, and a cation selective side (not shown) facing the cathode. The electrolysis cell 10 illustrated in FIG. 1 comprises four compartments: an anolyte compartment 16 containing the anode 11 and separated from the remainder of the unit cell by the bipolar membrane 13; a catholyte compartment 19 containing the cathode 12 and separated from the remainder of the unit cell by the second divider 15; an internal compartment 17 located between the bipolar membrane 13 and the first divider 14; the second internal compartment 18 between the first divider 14 and the second divider 15.

In operation of the electrochemical cell illustrated in FIG. 1, a solution of an onium salt such as tetra n-butyl ammonium chloride (or an impure onium hydroxide such as tetra n-butyl ammonium hydroxide) is charged to the compartment 18 formed by the first divider and the second divider, and a liquid electrolyte such as an organic salt, water or a mixture of an organic salt and water is charged to the other compartments. An electrical potential is established and maintained between the anode and the cathode to produce a flow of current across the cell whereupon the quaternary ammonium cation is attracted to the cathode and passes through the second divider 15 into the catholyte compartment 19. The quaternary ammonium cation combines with the hydroxide ion formed at the cathode to produce the desired quaternary ammonium hydroxide. The anion of the quaternary ammonium salt is attracted to the anode and passes through the first divider 14 to compartment 17 where the anion combines with a hydrogen cation produced at the bipolar membrane. An acid is formed in compartment 17 which can be covered. When the quaternary ammonium salt is charged to compartment 18 in FIG. 1 is tetra n-butyl ammonium chloride, tetra n-butyl ammonium hydroxide is formed and recovered from the catholyte compartment 19, and hydrochloric acid is recovered from compartment 17.

In another embodiment, the unit cell is similar to the cell shown in FIG. 1 and comprises four compartments defined by, in sequence, beginning at the anode, a bipolar membrane, an anion selective membrane and a cation selected membrane, said bipolar membrane having an anion selective side facing the anode and a cation selective side facing the cathode. This arrangement is referred to herein as the BAC arrangement (bipolar/anion selective/ cation selective membranes).

Figure 2:
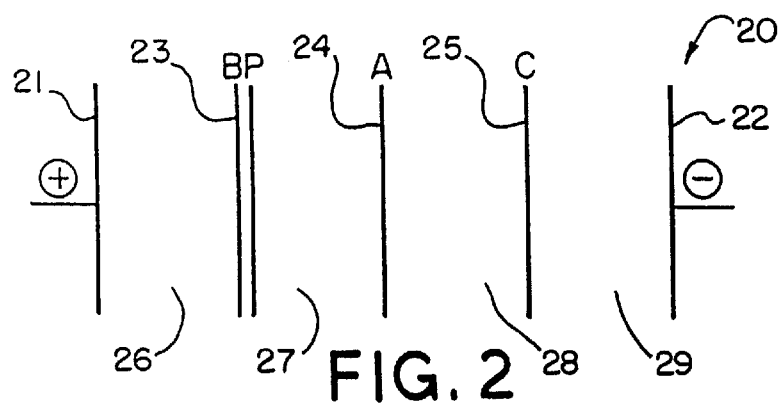
FIG. 2 is a schematic representation of another electrolytic cell similar to FIG. 1.

An electrolytic cell utilizing the BAC unit cell is illustrated in FIG. 2 which is a schematic representation of an electrolytic cell 20 comprising an anode 21, a cathode 22 and a unit cell comprising in sequence, beginning at the anode 21, a bipolar membrane 23, an anion selective membrane 24, and a cation selective membrane 25. The bipolar membrane 23 has an anion selective side (not shown) facing the anode, and a cation selective side (not shown) facing the cathode. The electrolytic cell 20 illustrated in FIG. 2 comprises four compartments: an anolyte compartment 26 containing the anode 21 and separated from the remainder of the unit cell by the bipolar membrane 23; a catholyte compartment 29 containing the cathode 22 and separated from the remainder of the unit cell by the cation selective membrane 25; an internal compartment 27 located between the bipolar membrane 23 and the anion selective membrane 24; and a second internal compartment 28 between the anion selective membrane 24 and the cation selective membrane 25.

In operation of the electrolytic cell illustrated in FIG. 2, a solution of an onium salt such as tetramethylammonium chloride (or an impure onium hydroxide) in an electrolyte, preferably water is charged to compartment 28 formed by the anion selective membrane and the cation selective membrane. A liquid electrolyte such as an organic solvent, water or a mixture of an organic solvent and water is charged to the other compartments. Generally, the liquid electrolytes will comprise oxidizable liquids which can react at the anode. Examples of such oxidizable liquids include water, alcohols such as methanol, ethanol, propanol, ethylene glycol and diethylene glycol, hydrocarbons such as hexane, heptane, benzene, toluene, xylene, etc. Mixtures of such liquids may be utilized. Water, alcohols or mixtures of water and alcohols are preferred, and water is the most preferred example of a liquid electrolyte useful in the present invention. The concentration of the quaternary ammonium salt in the solution charged to the compartment defined by the anion selective membrane and the cation selective membrane is generally in the range of from about 3% to about 55% by weight, more often in the range of 5% to about 40% by weight.

After the solution of the quaternary ammonium salt (or the impure onium hydroxide) and the liquid electrolyte have been charged to the indicated compartments of the unit cell, an electrical potential is established and maintained between the anode and the cathode to produce a flow of current across the cell whereupon the quaternary ammonium cation passes through the cation selective membrane and into the catholyte compartment 29. The quaternary ammonium cation combines the hydroxide ion formed at the cathode to produce the desired quaternary ammonium hydroxide. The anion of the quaternary ammonium salt passes through the anion selective membrane 24 into compartment 27 where the anion combines with a proton produced at the bipolar membrane. An acid is formed in compartment 27 which can be recovered. When the quaternary ammonium salt charged to compartment 28 in FIG. 2 is tetramethylammonium chloride, tetramethylammonium hydroxide is formed in and recovered from the catholyte compartment 29 and hydrochloric acid is recovered from compartment 27.

Figure 2A:
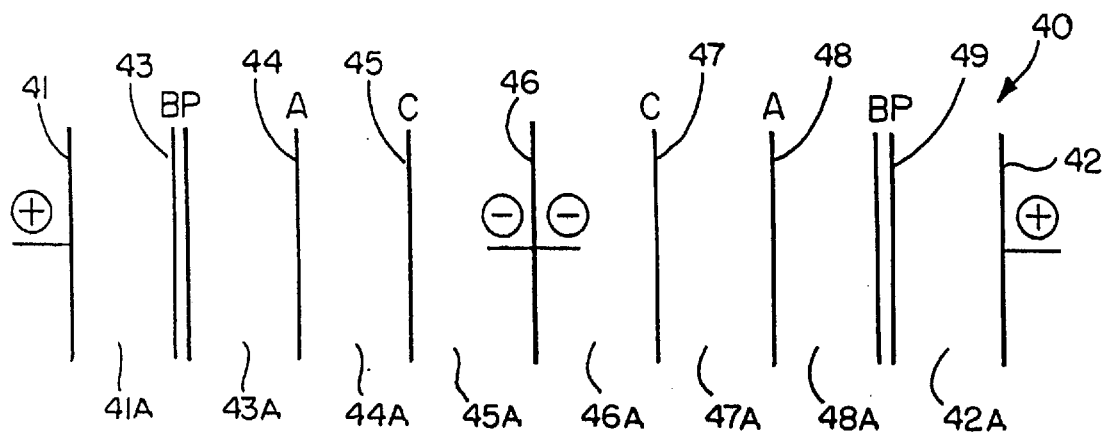
FIG. 2A is a schematic representation of an electrolytic cell containing a stack of two units of the unit cell of FIG. 2 in a monopolar configuration.

The electrochemical cells useful in this invention may comprise stacks of two or more unit cells arranged for electrolysis or electrodialysis. FIG. 2A illustrates an electrolytic cell containing a stack of two unit cells in a monopolar configuration, and FIG. 2B illustrates an electrolyte cell containing 2 unit cells in a bipolar configuration.

In particular, FIG. 2A illustrates an electrolysis cell comprising a stack of two BAC unit cells in a monopolar configuration. The electrolytic cell 40 comprises a pair of anodes 41 and 42, a two sided cathode 46, and eight compartments (41A–48A) which are defined by in sequence beginning at the anode 41, a first bipolar membrane 43, a first anion selective membrane 44, a first cation selective membrane 45, the cathode 46, a second cation selective membrane 47, a second anion selective membrane 48, and a second bipolar membrane 49. The two bipolar membranes 43 and 49 are arranged to have an anion selective side (not shown) facing the anode and a cation selective side (not shown) facing the cathode in each unit cell.

In the embodiment of the electrolytic cell illustrated in FIG. 2A, a solution (preferably aqueous) of the onium salt is charged to compartments 44A and 47A which are defined by the first anion selective membrane 44 and the first cation selective membrane 45, and the second cation selective membrane 47 and the second anion selective membrane 48, respectively. Liquid electrolytes (as described above) are charged to the remaining compartments. After a current has been passed through the cell, the desired onium hydroxide is recovered from compartments 45A and 46A. Acid is recovered from compartments 43A and 48A.

Figure 2B:
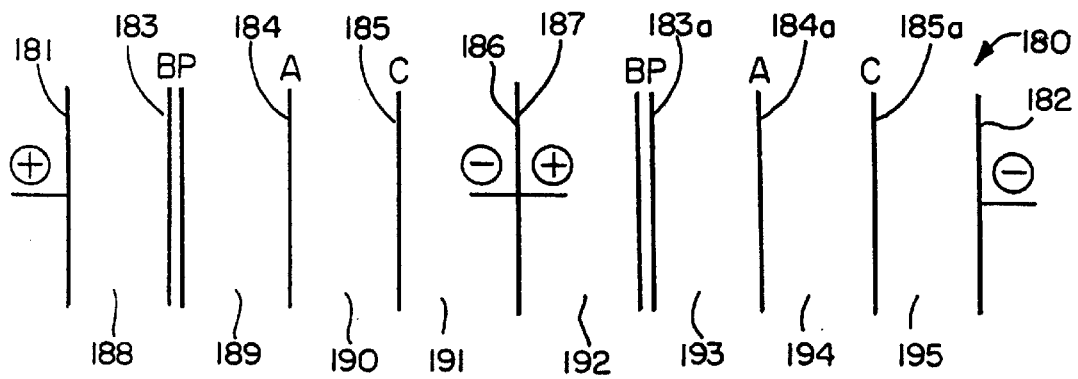
FIG. 2B is a schematic representation of an electrolytic cell containing a stack of two units of the unit cell of FIG. 2 in a bipolar configuration.

FIG. 2B illustrates an electrolyte cell comprising a stack of two BAC unit cells in a bipolar configuration. The electrolytic cell 180 comprises a pair of anodes 181 and 187, a pair of cathodes 186 and 182, and eight compartments (188–195) which are defined by, in sequence beginning at the anode 181, a first bipolar membrane 183, a first onium selective membrane 184, a first cation selective membrane 185, a cathode 186 and an anode 187 which are joined together a second bipolar membrane 183(a), a second anion selective membrane 184(a), and a second cation selective membrane 185(a). Each of the two bipolar membranes is arranged to have an anion selective side facing the anode and a cation selective side facing the cathode in each unit cell. The electrolytic cell of FIG. 2B is operated in generally the same manner as the cell of FIG. 2A.

Figure 2C:
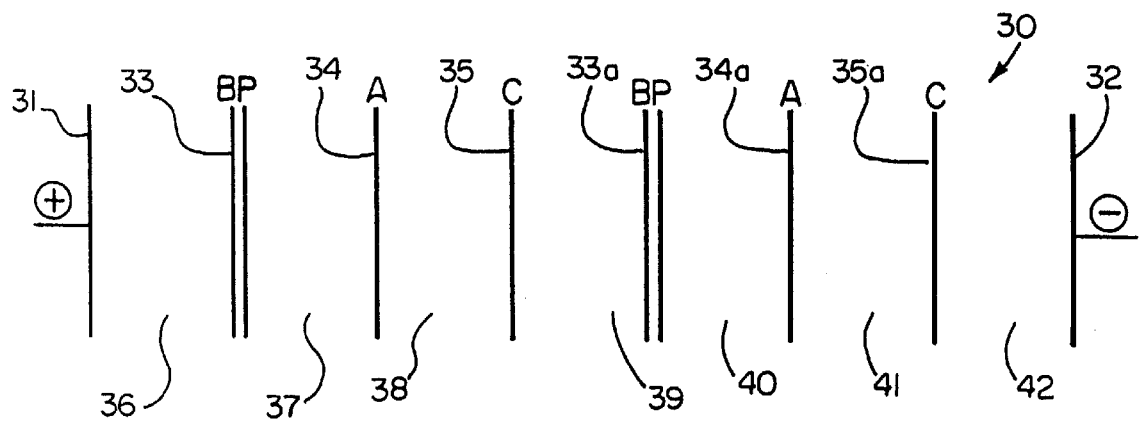
FIG. 2C is a schematic representation of an electrodialytic cell containing a stack of two units of the unit cell of FIG. 2.

FIG. 2C illustrates an electrodialytic cell comprising a stack of two BAC unit cells. The electrodialytic cell comprises an anode 31, a cathode 32 and seven compartments 36–42 which are defined by, in sequence beginning at the anode 31, a first bipolar membrane 33, a first anion selective membrane 34, a first cation selective membrane 35, a second bipolar membrane 33a, a second anion selective membrane 34a, and a second cation selective membrane 35a. The two bipolar membranes 33 and 33a are arranged to have the anion selective side (not shown) facing the anode 31 and the cation selective side (not shown) facing the cathode 32.

In the embodiment of the electrodialytic cell illustrated in FIG. 2C, a solution of the onium salt (preferably aqueous) is charged to compartments 38 and 41 which are defined by the first anion selective membrane and the first cation selective membrane, and the second anion selective membrane and the second cation selective membrane, respectively, and liquid electrolytes (as described above) are charged to the remaining compartments. After a current has been passed through the cell, the desired onium hydroxide is recovered from compartment 39 defined by the first cation selective membrane and the second bipolar membrane, and catholyte compartment 42 (defined by the second cation selective membrane and the cathode). Acid is recovered from compartment 37 defined by the first bipolar membrane and the first anion selective membrane, and compartment 40 defined by the second bipolar membrane 33a and the second anion selective membrane 34a.

Figure 3:
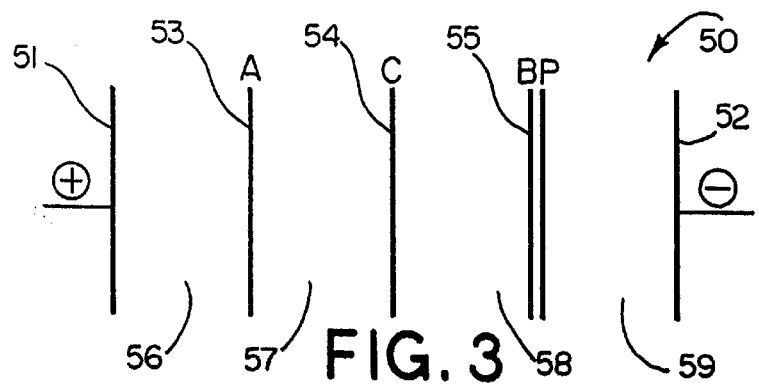
FIG. 3 is a schematic representation of another four-compartment electrolytic cell containing one unit cell.
Figure 3A:
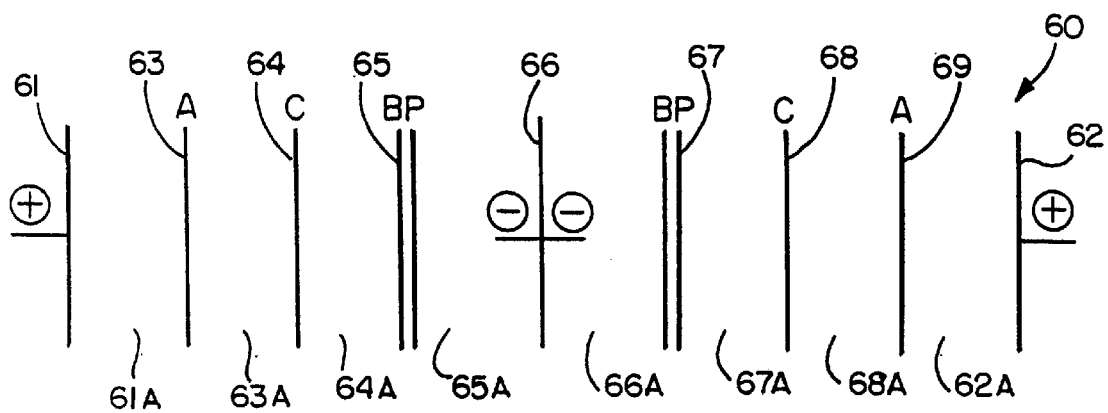
FIG. 3A is a schematic representation of an electrolytic cell containing a stack of two units of the unit cell of FIG. 3 in a monopolar configuration.
Figure 3B:
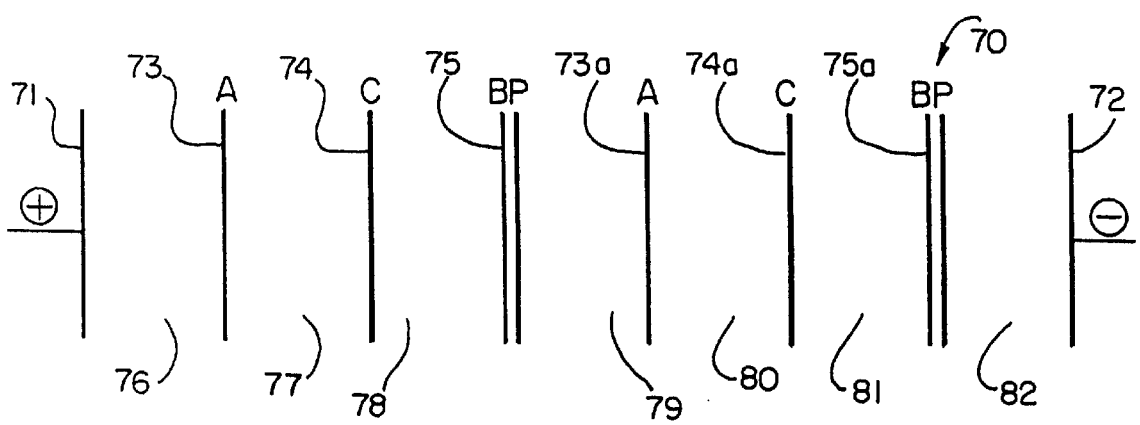
FIG. 3B is a schematic illustration of an electrodialytic cell containing a stack of two unit cells of FIG. 3.

Other electrochemical cells useful in the process of the present invention are illustrated in FIGS. 3, 3A and 3B. The cell shown in FIG. 3 comprises one unit cell and the cells illustrated in FIGS. 3A and 3B illustrate two unit cells, wherein the unit cell comprises four compartments defined by, in sequence beginning at the anode, an anion selective membrane, a cation selective membrane and a bipolar membrane (ACB configuration). In particular, the electrolytic cell 50 illustrated in FIG. 3 comprises an anode 51, a cathode 52 and a unit cell assembled for operational positioning between the anode and the cathode. The electrolytic cell of FIG. 3 comprises four compartments (56–59) which are defined by, in sequence beginning at the anode 51, an anion selective membrane 53, a cation selective membrane 54 and a bipolar membrane 55. The bipolar membrane 55 has an anion selective side (not shown) facing the anode 51 and a cation selective (not shown) facing the cathode 52. Compartment 56 may be referred to as the anolyte compartment and compartment 59 may be referred to as the catholyte compartment. In the embodiment illustrated in FIG. 3, an aqueous solution of an onium salt is charged to compartment 57 which is defined by the anion selective membrane 53 and the cation selective membrane 54. After a current is passed through the cell, the desired onium hydroxide product is recovered from compartment 58 which is defined by the cation selective membrane 54 and the bipolar membrane 55. Acid (for example, hydrochloric acid) is recovered from the anolyte compartment 56.

FIG. 3A illustrates an electrolysis cell 60 comprising two unit cells of the ACB configuration illustrated in FIG. 3 in a monopolar configuration. The electrolytic cell 60 of FIG. 3A comprises a first anode 61, a second anode 62, a cathode 66 and two unit cells resulting in the presence of eight compartments identified as 61A through 68A. The compartments are defined by, in sequence, beginning at the anode 61, a first anion selective membrane 63, a first cation selective membrane 64, a first bipolar membrane 65, a cathode 66, a second bipolar membrane 67, a second cationic selective membrane 68, and a second anion selective membrane 69. In this embodiment, a solution (preferably aqueous) of an onium salt is charged to compartments 63A and 68A, and a liquid electrolyte is charged to the remaining compartments. After a current is passed through the cell, the desired onium hydroxide is recovered from compartment 64A and compartment 67A. Acid is recovered from the anolyte compartments 61 A and 62A.

FIG. 3B illustrates an electrodialytic cell useful in the present invention which comprises a stack of two unit cells of the ACB configuration. The electrodialytic cell 70 of FIG. 3B comprises an anode 71, a cathode 72 and two unit cells resulting in the presence of seven compartments 76–82. The compartments are defined by, in sequence beginning at the anode 71, a first anion selective membrane 73, a first cation selective membrane 74, a first bipolar membrane 75, a second anion selective membrane 73a, a second cation selective membrane 74a and a second bipolar membrane 75a. In this embodiment, an aqueous solution of onium salt is charged to compartment 77 defined by the anion selective membrane 73 and the cation selective membrane 74 and to compartment 80 defined by the second anion selective membrane 73a and the second cation selective membrane 74a. A liquid electrolyte is charged to the remaining compartments, and after a current is passed through the cell, the desired onium hydroxide is recovered from compartment 78 defined by the first cation selective membrane and the first bipolar membrane and compartment 81 defined by the second cation selective membrane and the second bipolar membrane. Acid is recovered from compartments 76 and 79.

Figure 4:
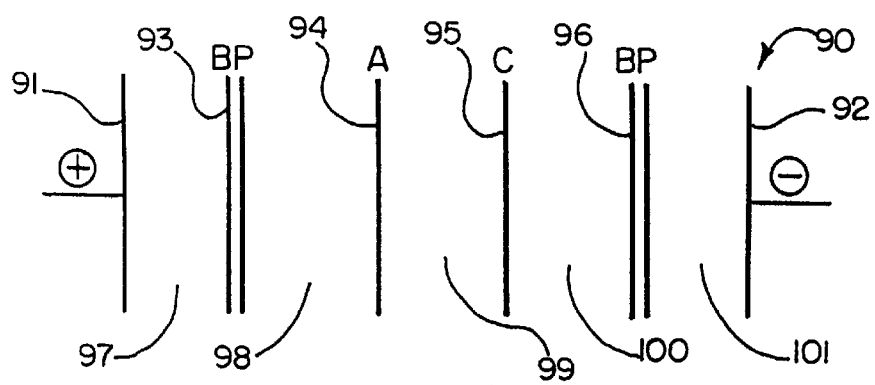
FIG. 4 is a schematic illustration of a five-compartment electrolytic cell containing one unit cell.
Figure 4A:
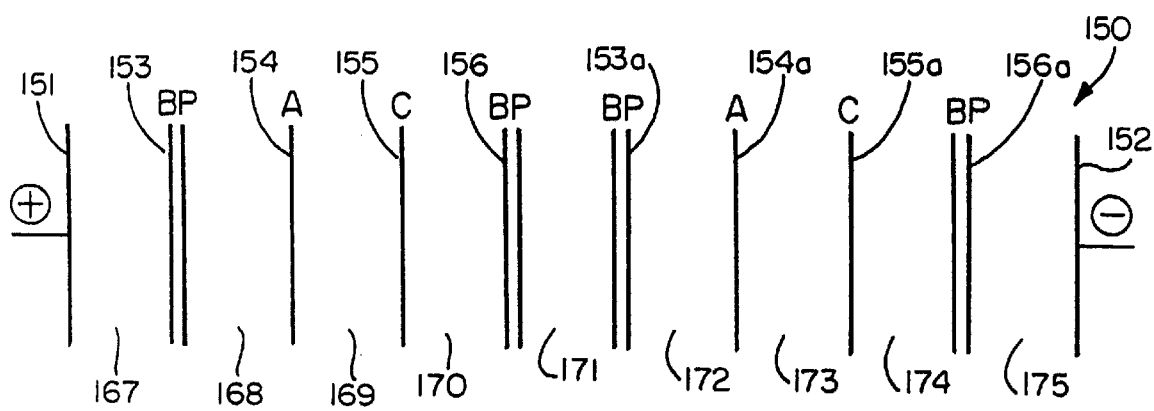
FIG. 4A is a schematic illustration of an electrodialytic cell containing a stack of two of the unit cells of FIG. 4.

Other examples of useful electrochemical cells comprising a different unit cell arrangement are illustrated in FIGS. 4 and 4A. In these embodiments, the membranes of the unit cells are arranged in the sequence bipolar membrane/anion selective membrane/cation selective membrane/bipolar membrane. This unit cell arrangement is referred to herein as the BACB arrangement.

More particularly, FIG. 4 illustrates an electrolysis cell 90 comprising an anode 91 and a cathode 92 and a unit cell comprising five compartments 97–101 which are defined by, in sequence beginning at the anode 91, a first bipolar membrane 93, an anion selective membrane 94, a cation selective membrane 95, and a second bipolar membrane 96. FIG. 4A illustrates an electrodialytic cell 150 comprising an anode 151 and a cathode 152 and two stacked unit cells of the BACB configuration resulting in nine compartments 167–175. The nine compartments are defined by, in sequence beginning at the anode 151, the first bipolar membrane 153, a first anion selective membrane 154, a first cation selective membrane 155, a second bipolar membrane 156, a third bipolar membrane 153a, a second anion selective membrane 154a, a second cation selective membrane 155a, and a fourth bipolar membrane 156a. As in the embodiments described above, the bipolar membranes are arranged to have an anion selective side (not shown) facing the anode 151 and a cation selective side (not shown) facing the cathode 152.

In the operation of the embodiment illustrated in FIG. 4A, a solution of an onium salt (preferably aqueous) is charged (a) to compartment 169 defined by the first anion selective membrane 154 and the first cation selective membrane 155, and (b) to compartment 173 defined by the second anion selective membrane 154a and the second cation selective membrane 155a. A liquid electrolyte is charged to the remaining compartments, and after a current is passed through the cell, the desired onium hydroxide is recovered from compartments 170 and 174. Acid is recovered from compartments 168 and 172. Compartment 171 defined by the second bipolar membrane and the third bipolar membrane forms a buffer region which separates the acid compartments from the quaternary ammonium hydroxide product compartment 170 thereby reducing contamination of the desired quaternary ammonium hydroxide by the acid anions.

Figure 5:
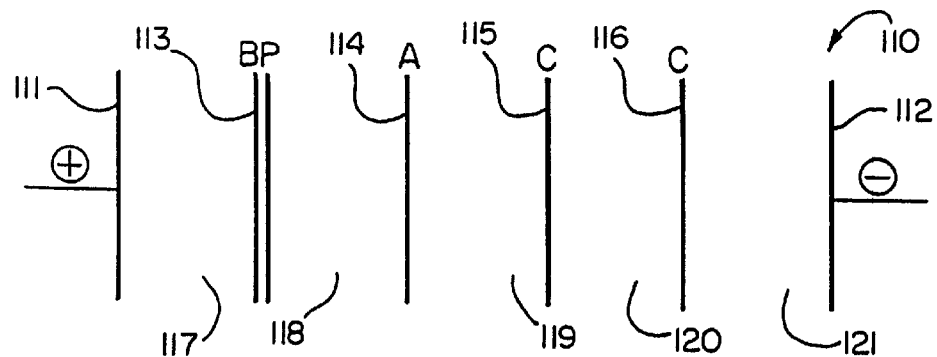
FIG. 5 is a schematic illustration of another example of a five-compartment electrolytic cell containing one unit cell.

Another unit cell configuration is illustrated in the electrochemical cell represented in FIG. 5. The unit cell comprises, in sequence beginning at the cathode, a bipolar membrane, an anion selective membrane, a first cation selective membrane and a second cation selective membrane, and this sequence is identified as BACC. More particularly, with regard to the electrodialytic cell 110 illustrated in FIG. 5, the cell comprises an anode 111, a cathode 112 and five compartments 117–121 which are defined by, in sequence beginning at the anode 111, a bipolar membrane 113, an anion selective membrane 114, a first cation selective membrane 115, and a second cation selective membrane 116. The bipolar membrane 113 has an anion selective side (not shown) facing the anode 111 and a cation selective side (not shown) facing the cathode 112. In the embodiment illustrated in FIG. 5, an aqueous solution of an onium salt is charged to compartment 119 defined by the anion selective membrane 114 and the first cation selective membrane 115. A liquid electrolyte is charged to the other compartments, and after a current is passed through the cell, the desired onium hydroxide is recovered from compartment 121 defined by the second cation selective membrane 116 and the cathode 112 (the catholyte compartments). Acid is recovered from compartment 118.

Figure 6:
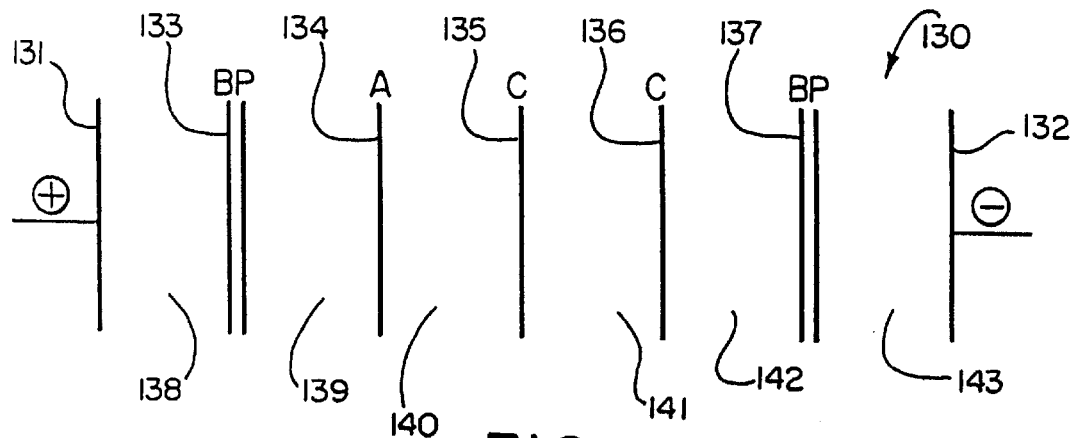
FIG. 6 is a schematic representation of an electrolytic cell comprising six compartments and one unit cell.

The embodiment of an electrochemical cell illustrated in FIG. 6 comprises a unit cell formed by, in sequence, a first bipolar membrane, an anion selective membrane, a first cation selective membrane, a second cation selective membrane, and a second bipolar membrane which can be referred to as the BACCB configuration. More particularly, the electrochemical cell 130 illustrated in FIG. 6 comprises an anode 131, a cathode 132, arid six compartments 138–143 defined by, in sequence beginning at the anode 131, a first bipolar membrane 133, an anion selective membrane 134, a first cation selective membrane 135, a second cation selective membrane 136 and a second bipolar membrane 137. The anion selective side (not shown) of each of the bipolar membranes faces the anode and the cation selective side (not shown) of the two bipolar membranes faces the cathode. In operation, a solution of the onium salt is charged to compartment 140 defined by the anion selective membrane 134 and the first cation selective membrane 135, and a liquid electrolyte is charged to the remaining compartments. After a current is passed through the cell, a solution of the desired onium hydroxide is recovered from compartment 142 which is defined by the second cation selected membrane 136 and the second bipolar membrane 137.

Operation of the process of the present invention utilizing the electrochemical cells illustrated in FIGS. 1–6 generally is continuous and all of the liquids are continuously recirculated. In each of the embodiments, a solution of an onium salt is charged to the compartment of each unit cell formed by an anion selective membrane and a cation selective membrane. Stated another way, the aqueous solution of the onium salt is charged to the compartment which is between the anion selective membrane and the cation selective membrane in each unit cell. The concentration of the onium salt in the aqueous solution charged to the cell is from about 3% to about 55% by weight and more often between 5% and 40% by weight.

Various materials can be used as anodes in the electrochemical cells. For example, the anode may be made of metals such as titanium-coated electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

The cathodes in the electrochemical cells utilized in the process of the present invention comprise any conductive material. Preferably the conductive metal is stable under the conditions present in the electrochemical cell (e.g. alkaline conditions), and the cathode comprises a material having a low overvoltage for hydrogen evolution. Some specific examples of materials useful as cathodes include stainless steel, nickel, titanium, graphite or carbon steel (iron).

The dividers or separators which can be utilized in the present invention can be selected from a wide variety of microporous diffusion barriers, screens, filters, diaphragms, etc., which contain pores of the desired size to allow the onium cations to migrate toward the cathode. The microporous dividers can be prepared from various materials including plastics such as polyethylene, polypropylene and Teflon, ceramics, etc. Specific examples of commercially available microporous separators include: Celanese Celgard and Norton Zitex. Microporous separators are particularly useful when the process of the present invention is utilized to prepare the higher molecular weight hydroxides such as tetra and butyl phosphonium hydroxide and tetra n-butyl ammonium hydroxide.

The cation selective membranes used in the cells and the process of the invention may be any of those which have been used in the electrolysis of onium salts to onium hydroxides. Preferably, the cation-exchange membranes should comprise a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic and/perfluorocarboxylic acid, perfluorocarbon polymer membranes such as sold by the E.I. dupont Nemours & Co. under the general trade designation "Nafion" such as DuPont's Cationic Nafion 902 membrane. Other suitable cation selective membranes include styrenedivinyl benzene copolymer membranes containing cation selective groups such as sulfonate groups, carboxylate groups, etc. Raipore Cationic R1010, (from Pall RAI), and NEOSEPTA CMH and NEOSEPTA CM1 membranes from Tokuyama Soda are useful particularly with the higher molecular quaternary salts. The preparation and structure of cation selective membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

Any anion selective membrane may be utilized including membranes used in processes for the desalination of brackish water. Preferably, membranes should be selective with respect to the particular anions present in the cell (e.g., halide ions). The preparation and structure of anionic membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various anionic membranes which may be useful in the process of the present invention.

Among the anion selective membranes which may be utilized and which are commercially available are the following: AMFLON, Series 310, based on fluorinated polymer substituted with quaternary ammonium groups produced by American Machine and Foundry Company; IONAC MA 3148, MA 3236 and MA 3475, based on polymer substituted with quaternary ammonium derived from heterogenous polyvinylchloride produced by Ritter- Pfaulder Corp., Permutit Division; Tosflex IE-SF 34 or IE-SA 48 made by Tosoh Corp. which is a membrane designed to be stable in alkaline media; NEOSEPTA AMH, NEOSEPTA ACM, NEOSEPTA AFN or NEOSEPTA ACLE-SP from Tokuyama Soda Co.; and Selemion AMV and Selemion AAV from Asahi Glass. In one embodiment, the Tosflex IE-SF 34 and NEOSEPTA AMH anion exchange membranes are preferred because of their stability in alkaline solutions such as the onium hydroxide solution which are formed in the process of the invention.

One of the advantages of the process of the present invention is that the process produces HCl rather than $Cl_2$ gas. The bipolar membrane utilized in the process of the present invention prevent the chloride anion from approaching the anode and thereby prevents chlorine gas formation. In the embodiment of FIGS. 5 and 6, higher purity quaternary ammonium hydroxide is obtained since the quaternary ammonium cation passes through two cation selective membranes resulting in lower contamination of the desired hydroxide by other anions such as chloride ion.

The bipolar membranes used in the electrochemical cells are composite membranes comprising three parts: a cation selective side or region, an anion selective side or region, and an interface between the two regions. When a direct current passes across a bipolar membrane, with the cation selective side toward or facing the cathode, electrical conduction is achieved by the transport of $H^+$ and $OH^-$ ions which are produced by the dissociation of water which occurs at the interface under the influence of an electrical field. Bipolar membranes are described, for example, in U.S. Pat. Nos. 2,829,095, 4,024,043 (single film bipolar membranes) and in 4,116,889 (cast bipolar membranes). The bipolar membranes useful in the process of the present invention include NEOSEPTA BIPOLAR 1 by Tokuyama Soda, WSI BIPOLAR, and Aqualytics Bipolar membranes.

The current which is passed through the electrochemical cell generally is a direct current of a voltage dictated by the design and performance characteristics of the cell which are readily apparent to those skilled in the art and/or can be determined by routine experimentation. Current densities between 0.1 and 1.5 amps per square inch are generally used, and current densities between 0.6 and 1.2 amps per square inch are preferred. Higher or lower current densities can be used for certain specific applications.

During the electrochemical process, it is generally desirable that the temperature of the liquids within the cell be maintained within the range of from about 10° C. to about 70° C. and more generally, the temperature is maintained at about 50° C. during the electrochemical process.

The following examples illustrate the process of the present invention. Unless otherwise indicated in the following examples and elsewhere in the specification and claims, all parts and percentages are by weight, all temperatures are in degrees Centigrade, and pressure is at or near atmospheric pressure. The electrochemical cell utilized in Examples 1–3 is a four-compartment cell similar to that shown in FIG. 2. The process is operated continuously by periodic addition of feed into the feed compartment, removal of product from the catholyte tank and addition of water into the acid compartment to maintain the acid concentration constant. The anolyte solution also is replenished periodically. The electrochemical cell used in Example 4 is a five-compartment cell as illustrated in FIG. 5.

EXAMPLE 1

The electrochemical cell used consists of four compartments defined by, in sequence, beginning at the anode, a bipolar membrane NEOSEPTA BIPOLAR 1, an anion selective membrane (NEOSEPTA AMH) and a cation selective membrane (RAIPORE R1010). The anode has a surface area of 16 in.$^2$ and is titanium mesh coated with ruthenium oxide. The cathode is stainless steel with a surface area of 16 in.$^2$. A solution of 8% hydrobromic acid is introduced into the acid compartment which is positioned between the bipolar membrane and the anion selective membrane. The anolyte is a solution of 12% tetrapropylammonium hydroxide. An aqueous solution of 25% by weight of tetrapropylammonium bromide is charged to the compartment defined by the anion selective membrane and the cation selective membrane. A small amount of tetrapropylammonium hydroxide (about 2% by weight) is mixed with the water in the catholyte compartment to improve conductivity. The process is operated in a continuous manner and the flow rates in all compartments are maintained at about 0.40 gallon/minute. The catholyte temperature is maintained at about 40° C., and the electrolysis is conducted at 10 amps with a cell voltage of 12 volts. An overall current efficiency of 50% is achieved. A solution of 20% tetrapropylammonium hydroxide containing about 40 ppm bromide is formed in and recovered from the catholyte compartment.

EXAMPLE 2

The general procedure of Example 1 is repeated except that an aqueous solution of 32% by weight of tetrabutylammonium bromide is charged into the feed compartment defined by the anion selective membrane and the cation selective membrane. A solution of 15% tetrabutylammonium hydroxide is introduced into the anolyte compartment, and a small amount of tetrabutylammonium hydroxide solution (about 2%) is mixed with the water in the catholyte compartment to improve the conductivity. The electrolysis is carried out at 10 amps and a cell voltage of 13 volts. A current efficiency of 40% is achieved, and the final product solution containing 26% tetrabutylammonium hydroxide and 50 ppm bromide is obtained.

EXAMPLE 3

The general procedure of Example 1 is repeated except that the cationic selective membrane RAIPORE R1010 is replaced with the cationic selective NAFION 902 made by DuPont. A solution of 28% tetramethylammonium chloride is introduced into the feed compartment defined by the anion selective membrane and the cation selective membrane. The anolyte compartment comprises a solution of 10% tetramethylammonium hydroxide, and a solution of 3.5% hydrochloric acid is introduced into the acid compartment. A small amount of tetramethylammonium hydroxide (about 2%) is mixed with the water in the catholyte compartment to improve the conductivity. The electrolysis is carried out at 10 amps and a cell voltage of 12 volts. An overall current efficiency of 90% is achieved, and a solution of 20% tetramethylammonium hydroxide with 2 ppm chloride is obtained in the catholyte compartment.

EXAMPLE 4

The electrochemical cell utilized in this example comprises five compartments and is similar to the electrochemical cell illustrated in FIG. 5. The five compartments are defined by, in sequence, beginning at the anode, a NEOSEPTA BIPOLAR 1 membrane, an anion selective membrane (NEOSEPTA ACM), a first cation selective membrane (NAFION 902) and a second cation selective membrane (NAFION 902). The anode has a surface area of 16 in.$^2$ and is made of titanium mesh coated with ruthenium oxide. The cathode is a stainless steel plate with a surface area of 16 in.$^2$. An aqueous solution of 20% tetramethylammonium chloride is introduced into the feed compartment defined by the anion selective membrane and the first cation selective membrane (compartment 119 in FIG. 5.) A solution of 3.5% hydrochloric acid in water is introduced into the acid compartment which is positioned between the bipolar membrane and the anion selective membrane. A solution of 15% by weight tetramethylammonium hydroxide in water is introduced into the compartment which is positioned between the first cation selective membrane and the second cation selective membrane. A small amount of tetramethylammonium hydroxide (about 2%) is mixed with water in the catholyte compartment to improve the conductivity. The flow rate in all compartments is maintained at about 0.4 gallon/minute. The catholyte temperature is controlled at about 40° C., and the electrolysis is carried out at 10 amps and a cell voltage of 14 volts. An overall current efficiency of 90% is achieved, and a solution of 20% tetramethylammonium hydroxide in water with 0.02 ppm chloride is obtained.

EXAMPLE 5

The general procedure of Example 1 is repeated except that an aqueous solution of 36% by weight of tetrabutylphosphonium chloride is charged into the feed compartment defined by the anion selective membrane and the cation selective membrane. A solution of 17% tetrabuthylphosphonium hydroxide is introduced into the anolyte compartment, and a small amount of tetrabuthylphosphonium hydroxide solution (about 2%) is mixed with the water in the catholyte compartment to improve the conductivity. The electrolysis is carried out at 5 amps and a cell voltage of 9.0 volts. A current efficiency of 40% is achieved, and the final product solution containing 34% tetrabuthylphosphonium hydroxide with 50 ppm chloride is obtained.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for preparing an onium hydroxide from a corresponding onium salt in an electrochemical cell which comprises the steps of:
   (A) providing a cell comprising an anode, a cathode and one or more unit cells assembled for operational positioning between the anode and the cathode, each unit cell comprising:
      (A-1) four compartments defined by, in sequence beginning at the anode, a bipolar membrane, a first divider and a second divider, said bipolar membrane having an anion selective side facing the anode and a cation selective side facing the cathode; or
      (A-2) four compartments defined by, in sequence beginning at the anode, a first divider, a second divider, and a bipolar membrane having an anion selective side facing the anode and a cation selective side facing the cathode; or
      (A-3) five compartments defined by, in sequence beginning at the anode, a first bipolar membrane, a first divider, a second divider, and a second bipolar membrane, each of said bipolar membranes having an anion selective side facing the anode and a cation selective side facing the cathode; or
      (A-4) five compartments defined by, in sequence beginning at the anode, a bipolar membrane, a first divider, a second divider, and a third divider facing the anode and a cation selective side facing the cathode; or
      (A-5) six compartments defined by, in sequence beginning at the anode by a first bipolar membrane, a first divider, a second divider, a third divider, and a second bipolar membrane, each of said bipolar membranes having an anion selective side facing the anode and a cation selective side facing the cathode;
   (B) charging a solution of the onium salt to the compartment in each unit cell formed by the first and second dividers;
   (C) charging a liquid electrolyte to the other compartments of each unit cell;
   (D) passing a current through the cell to produce the onium hydroxide in the compartment in each unit cell formed by one of the dividers on the anode side and a bipolar membrane on the cathode side, or the compartment formed by a divider and the cathode; and
   (E) recovering the onium hydroxide from said compartments, wherein the onium salt is selected from the group consisting of halide, sulfate, hydrogen sulfate, nitrate, carbonate, phosphate, hydrogen phosphate and dihydrogen phosphate.

2. The process of claim 1 wherein
   (F) an acid is recovered from the compartments formed by a bipolar membrane on the anode side and the first divider on the cathode side and the compartments formed by the anode and the first divider.

3. The process of claim 1 wherein the onium salt is a halide, sulfate, phosphate or carbonate salt.

4. The process of claim 1 wherein the onium salt is characterized by the formula

wherein A$^+$ is an ammonium, phosphonium or sulfonium cation, and X$^-$ is an anion selected from the group consisting of halide, sulfate, hydrogen sulfate, nitrate, carbonate, phosphate, hydrogen phosphate and dihydrogen phosphate.

5. A process for preparing an onium hydroxide from a corresponding onium salt in an electrochemical cell which comprises the steps of:
   (A) providing a cell comprising an anode, a cathode and one or more unit cells assembled for operational positioning between the anode and the cathode, each unit cell comprising:
      (A-1) four compartments defined by, in sequence beginning at the anode, a bipolar membrane, an anion selective membrane and a cation selective membrane, said bipolar membrane having an anion selective side facing the anode and a cation selective side facing the cathode; or
      (A-2) four compartments defined by, in sequence beginning at the anode, an anion selective membrane, cation selective membrane, and a bipolar membrane having an anion selective side facing the anode and a cation selective side facing the cathode; or
      (A-3) five compartments defined by, in sequence beginning at the anode, a first bipolar membrane, an anion selective membrane, a cation selective membrane, and a second bipolar membrane, each of said bipolar membranes having an anion selective side facing the anode and a cation selective side facing the cathode; or (A-4) five compartments defined by, in sequence beginning at the anode, a bipolar membrane, an anion selective membrane, a first cation selective membrane, and a second cation selective membrane, said bipolar membrane having an anion selective side facing the anode and a cation selective side facing the cathode; or (A-5) six compartments defined by, in sequence beginning at the anode by a first bipolar membrane, an anion selective membrane, a first cation selective membrane, a second cation selective membrane, and a second bipolar membrane, each of said bipolar membranes having an anion selective side facing the anode and a cation selective side facing the cathode;

(B) charging a solution of the onium salt to the compartment in each unit cell formed by an anion selective membrane and a cation selective membrane;

(C) charging a liquid electrolyte to the other compartments of each unit cell;

(D) passing a current through the cell to produce the onium hydroxide in the compartment in each unit cell formed by a cation selective membrane on the anode side and a bipolar membrane on the cathode side, or the compartment formed by a cation selective membrane and the cathode; and (E) recovering the onium hydroxide from said compartments, wherein the onium salt is selected from the group consisting of halide, sulfate, hydrogen sulfate, nitrate, carbonate, phosphate, hydrogen phosphate and dihydrogen phosphate.

6. The process of claim 5 wherein an acid is recovered from the compartments formed by a bipolar membrane on the anode side and an anion selective membrane on the cathode side and the compartments formed by the anode and an anion selective membrane.

7. The process of claim 5 wherein the onium salt is a halide, sulfate, phosphate or carbonate salt.

8. The process of claim 5 wherein the onium salt is characterized by the formula $$A^+X^-$$

wherein $A^+$ is an ammonium, phosphonium or sulfonium cation, and $X^-$ is an anion selected from the group consisting of halide, sulfate, hydrogen sulfate, nitrate, carbonate, phosphate, hydrogen phosphate and dihydrogen phosphate.

9. The process of claim 8 wherein $X^-$ is a halide, sulfate, phosphate or carbonate anion.

10. The process of claim 5 wherein the onium salt is a quaternary onium salt characterized by the formula

(I)

wherein A is a nitrogen or a phosphorus atom, $R^1$, $R_2$, $R^3$ and $R^4$ are each independently alkyl groups containing from 1 to about 20 carbon atoms, hydroxy alkyl or alkoxy alkyl groups containing from 2 to about 20 carbon atoms, aryl groups, hydroxyaryl groups, or $R^1$ and $R^2$ together with A may form a heterocyclic group provided that if the heterocyclic group contains a C=A group, $R^3$ is the second bond, $X^-$ is an anion selected from the group consisting of halide, sulfate, hydrogen sulfate, nitrate, carbonate, phosphate, hydrogen phosphate and dihydrogen phosphate, and y is a number equal to the valence of X.

11. The process of claim 10 wherein $R^1$, $R^2$, $R^3$ and $R^4$ are each independently alkyl groups containing from 1 to about 20 carbon atoms.

12. The process of claim 11 wherein $R^1$, $R^2$, $R^3$ and $R^4$ are each independently methyl, ethyl, propyl or butyl groups.

13. The process of claim 10 wherein $X^-$ is a halide sulfate, phosphate or carbonate anion.

14. The process of claim 10 wherein A is nitrogen.

15. The process of claim 5 wherein the onium salt is a quaternary ammonium salt characterized by the formula

(II)

wherein $R_1$, $R_2$, $R_3$ and $R_4$ are each independently alkyl groups containing from 1 to 10 carbon atoms, hydroxyalkyl or alkoxyalkyl groups containing from 2 to about 10 carbon atoms, aryl groups or hydroxyaryl groups, X is an anion selected from the group consisting of halide sulfate, hydrogen sulfate, nitrate, carbonate, phosphate, hydrogen phosphate and dihydrogen phosphate, and y is a number equal to the valence of X.

16. The process of claim 15 wherein $X^-$ is a halide, sulfate, phosphate or carbonate anion.

17. The process of claim 15 wherein $R_1$, $R_2$, $R_3$ and $R_4$ are each independently alkyl groups containing 1 to 5 carbon atoms or hydroxyalkyl groups containing 2 to 5 carbon atoms.

18. The process of claim 5 wherein the concentration of onium salt in the solution charged in step (B) is from about 3% to about 55% by weight.

19. The process of claim 5 wherein each unit cell comprises:

(A-1) four compartments defined by, in sequence beginning at the anode, a bipolar membrane, an anion selective membrane and a cation selective membrane, said bipolar membrane having an anion selective side facing the anode and a cation selective side facing the cathode.

20. The process of claim 5 wherein each unit cell comprises:

(A-2) four compartments defined by, in sequence beginning at the anode, an anion selective membrane, a cation selective membrane and a bipolar membrane having an anion selective side facing the anode and a cation selective side facing the cathode.

21. The process of claim 5 wherein each unit cell comprises:

(A-3) five compartments defined by, in sequence beginning at the anode, a first bipolar membrane, an anion selective membrane, a cation selective membrane and a second bipolar membrane, each of said bipolar membranes having an anion selective side facing the anode and a cation selective side facing the cathode.

22. The process of claim 5 wherein each unit cell comprises:

(A-4) five compartments defined by, in sequence beginning at the anode, a bipolar membrane, an anion selective membrane, a first cation selective membrane and a second cation selective membrane, said bipolar membrane having an anion selective side facing the anode and a cation selective side facing the cathode.

23. The process of claim 5 wherein each unit cell comprises:

(A-5) six compartments defined by, in sequence beginning at the anode by a first bipolar membrane, an anion selective membrane, a first cation selective membrane, a second cation selective membrane and a second bipolar membrane, each of said bipolar membranes having an anion selective side facing the anode and a cation selective side facing the cathode.

24. The process of claim 5 wherein the liquid electrolyte charged to the other compartments of each unit cell comprises water.

25. A process for purifying an onium hydroxide in an electrochemical cell which comprises the steps of:
   (A) providing a cell comprising an anode, a cathode and one or more unit cells assembled for operational positioning between the anode and the cathode, each unit cell comprising:
      (A-1) four compartments defined by, in sequence beginning at the anode, a bipolar membrane, a first divider and a second divider, said bipolar membrane having an anion selective side facing the anode and a cation selective side facing the cathode; or
      (A-2) four compartments defined by, in sequence beginning at the anode, a first divider, a second divider, and a bipolar membrane having an anion selective side facing the anode and a cation selective side facing the cathode; or
      (A-3) five compartments defined by, in sequence beginning at the anode, a first bipolar membrane, a first divider, a second divider, and a second bipolar membrane, each of said bipolar membranes having an anion selective side facing the anode and a cation selective side facing the cathode; or
      (A-4) five compartments defined by, in sequence beginning at the anode, a bipolar membrane, a first divider, a second divider, and a third divider facing the anode and a cation selective side facing the cathode; or
      (A-5) six compartments defined by, in sequence beginning at the anode by a first bipolar membrane, a first divider, a second divider, a third divider, and a second bipolar membrane, each of said bipolar membranes having an anion selective side facing the anode and a cation selective side facing the cathode;
   (B) charging a solution consisting essentially of an impure onium hydroxide to be purified to the compartment in each unit cell formed by the first and second dividers;
   (C) charging a liquid electrolyte to the other compartments of each unit cell;
   (D) passing a current through the cell to produce the onium hydroxide in the compartment in each unit cell formed by one of the dividers on the anode side and a bipolar membrane on the cathode side, or the compartment formed by a divider and the cathode; and
   (E) recovering the onium hydroxide from said compartments.

26. A process for purifying an onium hydroxide in an electrochemical cell which comprises the steps of:
   (A) providing a cell comprising an anode, a cathode and one or more unit cells assembled for operational positioning between the anode and the cathode, each unit cell comprising:
      (A-1) four compartments defined by, in sequence beginning at the anode, a bipolar membrane, an anion selective membrane and a cation selective membrane, said bipolar membrane having an anion selective side facing the anode and a cation selective side facing the cathode; or
      (A-2) four compartments defined by, in sequence beginning at the anode, an anion selective membrane, cation selective membrane, and a bipolar membrane having an anion selective side facing the anode and a cation selective side facing the cathode; or
      (A-3) five compartments defined by, in sequence beginning at the anode, a first bipolar membrane, an anion selective membrane, a cation selective membrane, and a second bipolar membrane, each of said bipolar membranes having an anion selective side facing the anode and a cation selective side facing the cathode; or
      (A-4) five compartments defined by, in sequence beginning at the anode, a bipolar membrane, an anion selective membrane, a first cation selective membrane, and a second cation selective membrane, said bipolar membrane having an anion selective side facing the anode and a cation selective side facing the cathode; or
      (A-5) six compartments defined by, in sequence beginning at the anode by a first bipolar membrane, an anion selective membrane, a first cation selective membrane, a second cation selective membrane, and a second bipolar membrane, each of said bipolar membranes having an anion selective side facing the anode and a cation selective side facing the cathode;
   (B) charging a solution consisting essentially of an impure onium hydroxide to be purified to the compartment in each unit cell formed by an anion selective membrane and a cation selective membrane;
   (C) charging a liquid electrolyte to the other compartments of each unit cell;
   (D) passing a current through the cell to produce the onium hydroxide in the compartment in each unit cell formed by a cation selective membrane on the anode side and a bipolar membrane on the cathode side, or the compartment formed by a cation selective membrane and the cathode; and
   (E) recovering the onium hydroxide from said compartments.

* * * * *